United States Patent [19]

Atkinson

[11] Patent Number: 4,904,246

[45] Date of Patent: Feb. 27, 1990

[54] CANNULA ASSEMBLY

[75] Inventor: Robert W. Atkinson, Dover, Ohio

[73] Assignee: Snyder Laboratories, Inc., Dover, Ohio

[21] Appl. No.: 221,384

[22] Filed: Jul. 19, 1988

[51] Int. Cl.⁴ .............................................. A61M 25/00
[52] U.S. Cl. .................................... 604/264; 604/167; 604/256; 604/283
[58] Field of Search ............................... 604/158–169, 604/256, 264, 283

[56] References Cited

U.S. PATENT DOCUMENTS

| | | | |
|---|---|---|---|
| 2,687,731 | 8/1954 | Iarussi et al. | 604/256 |
| 4,211,214 | 7/1980 | Chikashige | 128/4 |
| 4,324,239 | 4/1982 | Gordon et al. | 604/256 |
| 4,436,519 | 3/1984 | O'Neill | 604/256 X |
| 4,655,752 | 4/1987 | Nonkanen et al. | 604/167 X |
| 4,673,393 | 6/1987 | Suzuki et al. | 604/256 X |
| 4,715,360 | 12/1987 | Akui et al. | 604/256 X |

Primary Examiner—Dalton L. Truluck
Attorney, Agent, or Firm—Paul David Schoenle

[57] ABSTRACT

A cannula assembly provides for fluid inflow at a scope end and to clear debris from the scope. An end fitting of the cannula assembly directs fluid flow in the direction of the scope end and also sealingly engages the scope to prevent fluid leakage.

2 Claims, 1 Drawing Sheet

U.S. Patent
Feb. 27, 1990
4,904,246
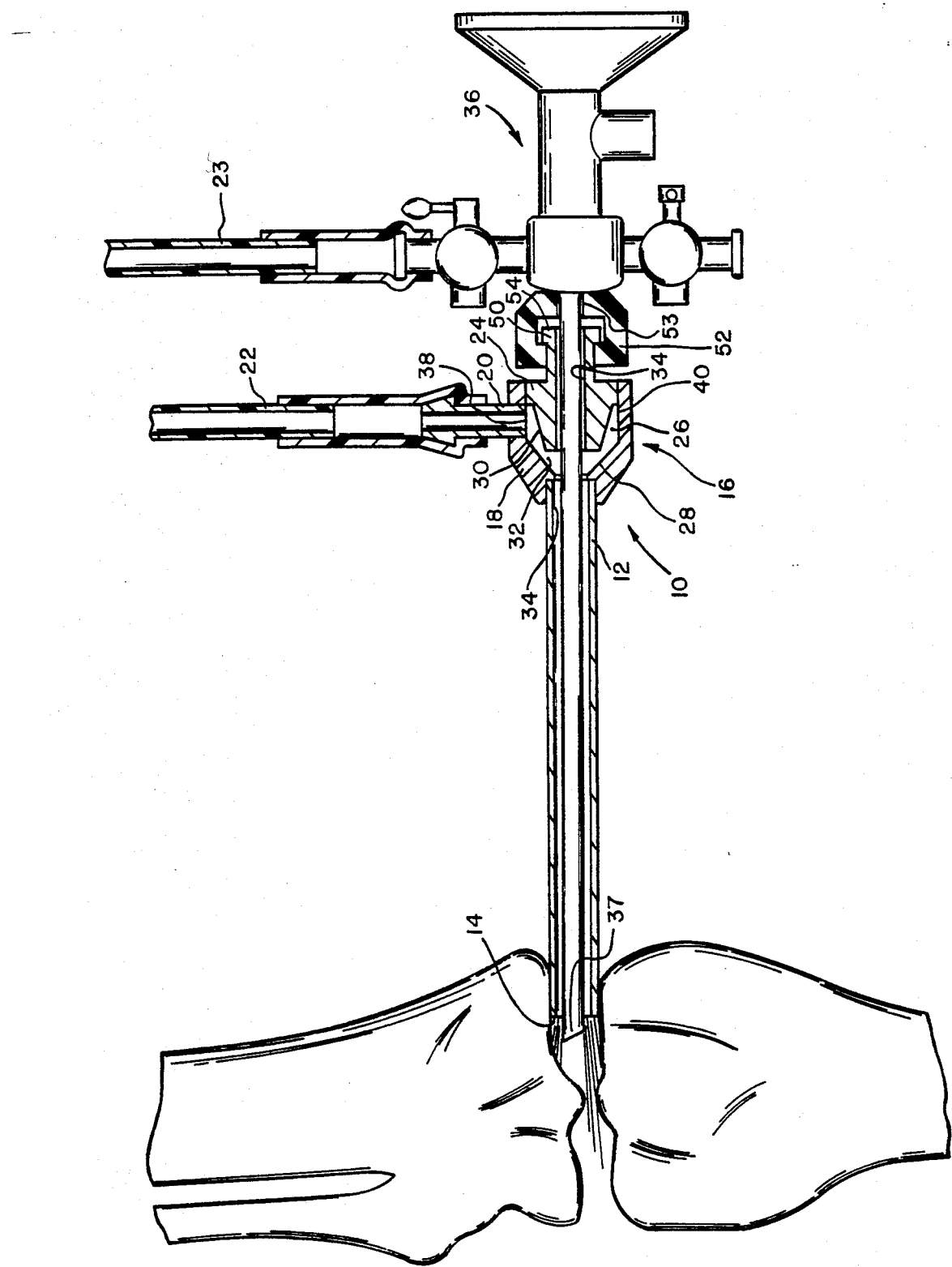

CANNULA ASSEMBLY

This invention relates to a cannula assembly wherein a sheath extends into a joint to enable a scope or instrument to be inserted into the sheath for observing the joint or performing arthroscopic surgery with the instrument inside the joint. The sheath cooperates with the scope or instrument to form a fluid path so that the joint is filled with fluid to expand the same during observation or surgery.

In the prior art, a joint required a first portal for a scope and a second portal for irrigation of the joint to distend the latter. Consequently, two incisions or openings were made at the location of the joint. With fluid pressure established in the joint it was necessary to provide an outlet for the fluid to remove debris and blood within the joint as a result of surgery. This fluid flow through the joint distorted the view of the joint at the scope so that observation of the joint during and following surgery was difficult.

The present invention provides an inflow cannula that is adapted for use with a scope. An end fitting defines in inlet port for fluid communication through the cannula and an inner frusto conical surface directs the fluid flow toward an outlet for uniform flow through the cannula. In addition, the end fitting carries a seal cooperating with the scope to seal the latter to the end fitting and cushion longitudinal movement between the scope and cannula, as well as center the scope within the end fitting.

With the inflow cannula of the present invention, the optic end of a scope, the monitor port and the fluid flow port to the joint are all disposed at the same location within the joint. Therefore, the fluid pump assembly senses the fluid pressure at the exact location of the optic lens.

It is an object of the present invention to provide an inflow cannula wherein fluid flow is directed toward the end of the cannula within a joint and a scope is sealingly disposed within the cannula.

In the drawing a cannula assembly is illustrated for observation of a knee joint.

During arthroscopic procedures, a small portal is established at the location in question and a cannula system 10 is inserted into the portal so that the tissue to be observed in the joint 11 is directly in front of the end of the cannula system.

The cannula system includes a tubular body or sheath 12 with an outlet 14 at one end and an end fitting 16 at an opposite end. The end fitting 16 includes a first part 18 secured to the sheath 12 and carrying an inlet nipple 20 coupled to a fluid pump assembly (not shown) via tubing 22. A second part 24 of the end fitting is secured via press fit with the first part to form a chamber 26 within the first part 18. The first part defines an inner frusto conical surface 28 and the second part defines an outer frusto conical surface 30. The surfaces 28 and 30 converge toward each other in the direction of the outlet 14 to a passage 32 in communication with a bore 34 extending longitudinally through the sheath and end fitting to receive a forward end of a scope 36. The scope includes an optic end 37 with a lumen extending from the joint 11 to a monitor tubing 23 communicating with the fluid pump assembly. The inlet nipple 20 defines an inlet port 38 intersecting an outer wall 40 extending between the surfaces 28 and 30 such that fluid entering the chamber 26 is directed by the surfaces 28 and 30 in the direction of the outlet 14 via bore 34. In other words the surfaces 28 and 30, and primarily surface 30, act as a baffle to direct fluid flow toward the outlet 14. The inner frusto conical surface 30 extends longitudinally past the inlet port 38 and the outer wall 40 toward the sheath 12 as it approaches the outer frusto conical surface 28 so that fluid entering chamber 26 will surround the outer frusto conical surface 30 and uniformly move in the direction of passage 32 and bore 34.

The second part 24 of the end fitting 16 includes a projection 50 extending outwardly from the chamber 26 to carry a seal 52 with an opening 53. The projection 50 forms a nipple with a flange 54 and the seal 52 is releasably trapped by the flange 54 to extend past the end of the projection 50. With the scope 36 disposed within the bore 34, the seal 52 sealingly engages the scope 36 to centrally position the scope within the end fitting. The seal inner diameter of opening 53 is smaller than an inner diameter for the portion of the bore 34 within the second part 24. In view of the length of the scope and sheath the scope at the outlet 14 will be capable of transverse movement; however, as the scope is inserted at the end fitting 16, the seal will assist in centering the scope as it is pushed through the end fitting. In addition the seal 52 covers the end of the projection 50 to cushion movement of the scope in the direction of the outlet 14, thereby avoiding banging of the scope against the end of the projection 50. The seal also protects the end of the scope 36 in the event the scope end hits the seal while attempting to insert the scope end through the seal opening 53.

In view of the aforegoing description, the present invention provides a cannula system for fluid inflow at the scope whereby fluid flow at the scope end carries debris away from the scope end to generate a cleaner view of the joint during arthroscopy.

I claim:

1. A cannula assembly comprising a tubular body with an end fitting at one end and an outlet at an opposite end, the body and end fitting defining a bore extending longitudinally therethrough in communication with the outlet for receiving a scope at the one end, the end fitting defining a chamber surrounding the scope when the latter is received within the body and end fitting, the end fitting defining an inlet port communicating fluid into the chamber, the end fitting defining an inner frusto conical surface leading to a passage communicating the chamber with the bore such that fluid communicated from the inlet to the chamber is directed by the inner frusto conical surface toward the passage and into the bore, the end fitting defining an outer frusto conical surface cooperating with the inner frusto conical surface to direct fluid flow from the inlet through the chamber toward the passage, and the outer frusto conical surface approaching the inner frusto conical surface toward the passage for uniform fluid flow from the inlet toward the outlet.

2. The cannula assembly of claim 1 in which the end fitting comprises a first part forming the outer frusto conical surface and a second part forming the inner frusto conical surface, the second part forming the inlet port, the first and second parts being secured together adjacent the inlet port to form the chamber therebetween and the first part defines a projection for carrying a seal engageable with the scope.

* * * * *